United States Patent [19]
Han et al.

[11] Patent Number: 6,020,538
[45] Date of Patent: Feb. 1, 2000

[54] GENETIC TRANSFORMATION OF ORCHIDS

[75] Inventors: Kyung-Hwan Han; Jaemo Yang, both of Kwangju, Rep. of Korea

[73] Assignee: Korea Kumho Petrochemical Co., Ltd., Seoul, Rep. of Korea

[21] Appl. No.: 09/071,204

[22] Filed: May 1, 1998

[51] Int. Cl.$^7$ .............................. C12N 15/82; C12N 15/31; C12N 15/54; C12N 15/65
[52] U.S. Cl. ......................... 800/293; 800/300; 800/323; 435/430; 435/470
[58] Field of Search .................................. 435/172.3, 419, 435/430, 470; 800/205, DIG. 62, 293, 300, 323

[56] References Cited

PUBLICATIONS

Chia et al. The firefly luciferase gene as a non–invasive reporter for Dendrobium transformation. The Plant Journal. 6(3):441–446, 1994.
Steinhart et al. Expression of the beta–glucuronidase reporter gene from a variety of promoter constructs in Cattleya protocorms and their protoplasts. Lindleyana: The Scientific Journal of the American Orchid Society. 12(4):172–179, Dec. 1997.
Seeni et al. Foliar regeneration of the endangered Red Vanda, Renanthera imschootiana Rolfe (Orchidaceae). Plant Cell, Tissue and Organ Culture. 29:167–172, 1992.
Badge et al. In vitro regeneration of Oncidium Gower Ramsey by high frequency protocorm like bodies proliferation. Indian Journal of Plant Physiology. 2(1):10–14, Jan–Mar. 1997.
Buising et al., *Mol. Gen. Genet.,* (1994) vol. 243, pp. 71–81.
McCabe et al., *Bio/Technology,* (Aug 1988) vol. 6.
Klein et al., *Nature,* (May 7, 1987) vol. 327, pp. 70–73.
Meyer et al., *Proc. Natl. Acad. Sci. USA*, (Nov. 1988) vol. 85, pp. 8568–8572.
Klein et al., *Proc. Natl. Acad. Sci. USA*, (Jun. 1988) vol. 85, pp. 4305–4309.
Hall, Jr. et al., *Proc. Natl. Acad. Sci. USA*, (Oct. 1991) vol. 88, pp. 9320–9324.
Kuehnle et al., *Plant Cell Reports*, (1992) vol. 11, No. 9, pp. 484–488.
Han et al., *Transgenic Research*, (1997) vol. 6, pp. 415–420.
Spiker et al., *Plant Physiol.*, (1996) vol. 110, pp. 15–21.
Chia et al., *The Plant Journal*, (1994) vol. 6, No. 3, pp. 441–446.

*Primary Examiner*—David T. Fox
*Attorney, Agent, or Firm*—Kenyon & Kenyon

[57] ABSTRACT

A method is disclosed for making genetically engineered orchid species using accelerated particle transformation. Meristem-tip tissue of orchid is cultured into a protocorm-like body (PLB). PLB is meristematic tissue and can be induced to regenerate into whole plant. In order to achieve efficient transformation it is necessary that relatively large numbers of meristematic cells are bombarded with the DNA-coated particles. After a particle-mediated transformation event, it is also important to stimulate continued meristemoid development before and during antibiotic selection and to reduce toxic effect of oxidized products of phenolics exuded after the wounding. It has been discovered that by using the techniques described in the present invention the meristematic tissue development, before and after the bombardment, can be stimulated while the toxic effect of oxidized phenolics can be reduced, resulting in successful transformation. The bombarded PLBs are multiplied and selected for the presence of gene products coded by the introduced genes. Shoot regeneration is then induced from the PLBs and transgenic seedlings are produced. Preferred plants for carrying out the present invention are the members of the genus Cymbidium.

10 Claims, 5 Drawing Sheets

GENETIC TRANSFORMATION OF ORCHIDS

BACKGROUND OF THE INVENTION

The present invention relates to the genetic engineering of plants in general and relates, in particular, to the method for transforming orchid species using particle-mediated transformation techniques.

There is substantial interest in genetic improvement of orchid species. Orchids are commercially grown globally and are the largest family of flowering plants with more than 800 genera and over 25,000 species. The potential for genetic modification of orchids for disease- and stress-resistance, inducing precocious flowering and developing varieties with modified flower color and morphology is of commercial importance. Conventional plant breeding methods for orchid improvement have been limited mainly due to the prohibitively long reproduction cycles (several years), slow seed maturation (several months), and difficulty of seedling analysis. Therefore, the possibility of employing genetic engineering techniques with orchids appears as an attractive alternative.

Genetic engineering is a means for inserting new genes that confer traits not readily available through conventional breeding. In contrast to sexual crosses, it allows new genes to be added while the genotypes of elite clones are retained intact. In order for genetic engineering approach to be successful, it is imperative to have an efficient gene transfer system for the given species. There are two means for the transformation of plants: use of biological vectors to deliver DNA to cells, primarily via a soil-dwelling plant pathogen bacterium Agrobacterium; and direct delivery of naked DNA into plant cells, primarily via particle bombardment.

The most widely used transformation technique to date is based on the use of the soil-born plant pathogen Agrobacterium, which has the innate ability to transfer a segment of DNA from their large endogenous Ti (tumor-inducing) or Ri (root-inducing) plasmids into an infected plant cell. However, successful application of the techniques depends on the host specific range of Agrobacterium. In the search for species- and genotype-independent transformation methods, several techniques based on the direct delivery of naked DNA to the plant cells were developed. These methods include electroporation, microinjection, PEG- or liposome-mediated DNA uptake, silicon carbide whiskers, and particle bombardment. Particle bombardment technique, also known as biolistics or microprojectiles, is based on the coating of DNA onto small carrier particles, which are then physically accelerated into plant cells. This method has several advantages. First, it does not require removal of cell walls for DNA entry. Second, DNA can be introduced into organized and differentiating cell masses such as meristems and adventitious buds. Third, manipulation of specialized biological plasmids is not required. Finally, DNA transfer does not depend on recognition and binding of a biological vector to cell membranes.

Current orchid propagation and breeding rely heavily on the culture of both seeds and protocorm-like bodies (PLBs) derived from shoot tip meristems. Protocorm, a storage organ, is formed from germinating embryo and possesses an apical meristem and a leaf primodium. PLB, also known as a somatic protocorm, is derived from in vitro culture of apical or axillary bud meristems and resembles the seedling protocorm both functionally and structurally. Such meristematic tissues may be suitable for particle bombardment and recovery of transgenic plants. It has been demonstrated in herbaceous plant species that those bombarded cells can be transformed in a fashion similar to Agrobacterium transformation (Klein et al., Proc. Natl. Acad. Sci. U.S.A., 88, pages 8502–8505, 1988). Germline cells of soybeans has been transformed by this particle-mediated transformation technique (McCabe et al., Bio/Technology, 6, pages 923–926, 1988). The U.S. Pat. No. 5,015,580 describes this technique. The U.S. Pat. No. 5,681,730 also describes the genetic engineering of somatic embryos and plants of gymnosperm species of tree through the use of particle bombardment. The advantage in this approach is that shoots develop directly from the primary and secondary meristems without an intervening explant-organogenesis phase. This minimizes treatment with phytohormones and thus opportunity for somaclonal variation.

Little information is available as to how the particle bombardment-mediated transformation methods might be applied to the transformation of orchids, particularly the members of genus Cymbidium. Currently, only two research papers concerning orchid transformation are available for the members of Dendrobium, none for Cymbidium that holds higher commercial value. Kuehnle and Sugii, Plant Cell Reports, 1992, reported obtaining transgenic Dendrobium. However, they did not show the expression of the screenable marker gene such as GUS. Furthermore, it was not known whether the transgenic plants were chimeric or not. Chia et al., Plant Journal, 1994, transformed Dendrobium orchid using particle bombardment. They developed an alternative selection method that relies on the expression of the introduced firefly luciferase gene, instead of antibiotic selection. In this system, light-emitting cell clumps were screened and isolated using a photon-counting video camera-photomultiplier system and high-power dissecting microscope. The whole screening and isolation process is repeated until a pure transgenic cell line is isolated. The isolated cell line is then induced to regenerate into whole plant. Because of the expensive equipment requirement, time-consuming and microscopic screening of transgenic cells, and the characteristic slow regeneration growth of orchids, this technique seems to be unrealistic for practical use of genetic transformation approach for orchid improvement.

Orchids are substantially different from other plants in their requirements for a transforming system. First, the orchid cells have a low rate of proliferation. Second, the orchid cells are recalcitrant to tissue cultural manipulations. Third, plant regeneration from de-differentiated cells has not been achieved for orchids. Fourth, the orchid cells are less sensitive to antibiotic selection. Orchid is known to be resistant to commonly used aminoglycosides such as kanamycin. It often requires higher than 500 mg/l kanamycin to select transgenic cells (Chia et al., Plant Journal, 1994). Fourth, the orchid cells in tissue culture exude a large quantity of phenolics, oxidized products of which are toxic to the cells. Finally, because of the multicellular structure of meristems, the resulting transgenic plants can sometime be chimeras with transformed and non-transformed sectors. One approach to obtain homogeneously transformed individuals from bombarded meristematic tissues is by selfing the treated generation and selecting for the added trait. The other is to insert DNA into meristematic tissues in early stages of organization and then stimulate continued meristemoid development during antibiotic selection. Application of these approaches to orchid transformation is limited mainly due to the long generation time and slow growth in tissue culture. Therefore, no protocol has been made available for practical use of genetic engineering techniques in orchids, particularly in the genus Cymbidium.

Accordingly, an object of the present invention is to provide an efficient method for transforming orchids, particularly the members of genus Cymbidium with particle bombardment. Another object of the present invention is to provide a method of stimulating continued meristemoid development before and after particle bombardment for transforming the developing protocorm-like bodies. Another object of the present invention is to provide a method of transforming protocorm-like bodies in which the tissues are capable of subsequently undergoing morphogenesis.

Another object of the present invention is to provide a methodology having broad applicability to the genetic engineering of orchids so that orchid improvement can be accelerated.

SUMMARY OF THE INVENTION

The methods disclosed herein can be used to produce a transformed orchid plant comprising transformed orchid cells, the transformed orchid cells containing a heterologous DNA construct comprising an expression cassette, which construct comprises, in the 5' to 3' direction, a transcription initiation region and a region which codes for a peptide positioned downstream from the transcription initiation region and under the transcriptional regulation thereof. The genetic engineering of orchids is achieved through the use of particle-mediated plant transformation technique in which tissue cultures of orchid species capable of plant regeneration are transformed with DNA carried on small carrier particles. It has been discovered that the culture technique described herein was shown to be useful in generating a relatively large number of meristematic cells to be bombarded, in stimulating continued development of the bombarded meristematic tissue, and subsequently in increasing the frequency of stable transformation. The bombarded meristematic tissues are proliferated and selected for the presence of gene products coded by the introduced genes. Shoot regeneration is then induced from the meristematic tissue and transgenic seedlings are produced. Preferred plants for carrying out the present invention are the members of the genus Cymbidium.

The objects, advantages, and features of the present invention will become apparent from the following specification when taken in conjunction with the accompanying drawings.

DETAILED DESCRIPTION OF THE INVENTION

In accordance with the present invention it has been discovered that the general approach of particle-mediated transformation of plant tissues can be successfully applied to orchids in tissue culture. This approach has enabled the creation of transgenic Cymbidium orchids. Since the technique which was used here is equally applicable to other orchids as well, it now becomes possible to genetically engineer orchids generally into transgenic orchid plants with characteristics favorable for disease resistance, modification of flowering time, manipulation of flower color and morphology, and other ornamental qualities. The process is believed applicable to all orchids and to Cymbidium orchids in particular.

The term orchid, as used herein, refers to a member of the order Orchidales in the phylum Spermatophyta. Exemplary orchids that may be used in practicing the present invention are the members of the Orchidaceae, which include, for example, the species in the genera of Acianthus, Aerides, Anoectochilus, Ansellia, Aplectrum, Arethusa, Calanthe, Cattleya, Coelogyne, Corallorhiza, Cymbidium, Cypripedium, Crytopodium, Dendrobium, Epidendrum, Goodyera, Listera, Macodes, Oncidium, Phalaenopsis, Pholidota, Rhynchostylis, and Vanda. Preferred for practicing the present invention are the members of Cymbidium.

The process described here relates to the introduction of exogenous genetic constructions into the genome of orchid plants. Such an exogenous genetic construction is preferably DNA from other organisms, whether of the same or different species, which is introduced into the cells of orchid through human manipulation. The exogenous genetic construction would normally include a coding sequence which codes for the production in the cells of the orchid of a transcription product or a protein of interest. The DNA construct typically includes flanking regulatory sequences effective to cause the expression of a protein, or the transcription product coded by the coding sequence, in the transformed cells of the orchid. Examples of flanking regulatory sequences are a promoter sufficient to initiate transcription in plant cells, and a terminator and/or polyadenylation sequence sufficient to terminate the gene product, whether by termination of transcription or translation. It is also possible to include translational enhancers located between the promoter and the coding sequence to assist in the efficiency of expression of the genetic product, especially in the expression of protein products. All of these regulatory regions should be capable of operating in the cells of the tissue to be transformed, either in a constitutive or a tissue-specific manner. The DNA construct may optionally include flanking DNA sequences that are involved in chromatin organization. Examples for such DNA sequences are matrix attachment regions (Spiker and Thompson, Plant Physiol., 1996), transformation booster sequences (Meyer et at., Proc. Natl. Acad. Sci. USA, 1988). Use of transformation booster sequences resulted in several fold increase in transformation frequencies using biolistics (Buising and Benbow, Mol. Gen. Genet., 1994). Use of flanking matrix attachment regions promoted the expression of the introduced genes in poplar (Han et al., Transgenic Research, 1997). It is also envisioned that gene products other than proteins may also be expressed in the inserted genetic construction. For example, the inserted construction can express an anti-sense RNA strand that is effective either to suppress the expression of an endogenous gene in the orchid or to inhibit a disease process by a pathogenic organism.

Genes of interest for use in orchids include a wide variety of phenotypic and non-phenotypic properties. Among the phenotypic properties are enzymes which provide for resistance to disease, modification of flowering time, control of plant color and morphology, manipulation of plant aroma, regulation of growth, and the like. Genes may be derived from prokaryotes or eukaryotes, bacteria, fungi, yeast, viruses, plants, and mammals or be synthesized in whole or in part.

One or more cassettes may be involved, where the cassettes may be employed in tandem for the expression of independent genes which may express products independently of each other or may be regulated concurrently, where the products may act independently or in conjunction. When multiple cassettes are employed, they may be on the same plasmid or on different plasmids. When the cassettes are on different plasmids, these plasmids may be carried by the same microprojectile, or they may be carried on different microprojectiles and these microprojectiles mixed together and propelled at the tissue target.

An expression cassette can be constructed which will include the transcriptional initiation region, the initiation codon, the coding sequence of the gene, the translational stop codons, followed by the transcriptional termination region. The direction is 5'-3' in the direction of transcription. The cassette will usually be of a length less than about 10 kilobases (kb), frequently less than about 6 kb, usually being at least about 1 kb. The expression cassette may be provided in a DNA construct which also has at least one replication system. For convenience, it is common to have a replication system functional in *Escherichia coli*. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids. In addition to the replication system, there will frequently be at least one marker present, which may be useful in one or more hosts, or different markers for individual hosts. That is, one marker may be employed for selection in a prokaryotic host, while another marker may be employed for selection in an eukaryotic host, particularly the orchid host. The markers may be protection against a biocide, such as antibiotics, toxins, heavy metals, or the like; provide complementation, by imparting prototrophy to an auxotrophic host; or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase, providing indigo production, luciferase, providing visible light production, NPTII, providing kanamycin resistance or G418 resistance, HPT, providing hygromycin resistance, and the mutated aroA gene, providing glyphosate resistance. The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Sambrook et al., Molecular Cloning: A Laboratory Manual, Cold Spring Harbor Laboratory, Cold Spring Harbor, N.Y., 1987.

Several instruments or apparatus for the introduction of such carrier particles into plant cells are known to those of ordinary skill in the art. Any ballistic cell transformation apparatus can be used in practicing the present invention. Exemplary apparatus is an instrument known as the Biolistics particle-acceleration instrument (model Biolistic PDS-1000/He) currently available from Bio-Rad Laboratories, 2000 Alfred Nobel Drive, Hercules, Calif. 94547 (telephone no. 510-741-1000). The device comprises a bombardment chamber, which is divided into two separate compartments by an adjustable-height stopping plate. An acceleration tube is mounted on top of the bombardment chamber. A macroprojectile is propelled down the acceleration tube at the stopping plate by an adjustable discharge of pressurized helium. The stopping plate has a bore hole formed therein which is smaller in diameter than the macroprojectile, the macroprojectile carries the microprojectile(s), and the macroprojectile is aimed and fired at the bore hole. When the stopping plate stops the macroprojectile, the microprojectile(s) are propelled through the bore hole. The target tissue is positioned in the bombardment chamber so that microprojectiles propelled through the bore hole penetrate the cell walls of the cells in the target tissue and deposit DNA constructs carried thereon in the cells of the target tissue. Exemplary materials from which the microprojectile may be formed include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The bombardment chamber is partially evacuated prior to use to prevent atmospheric drag from unduly slowing the microprojectiles. The chamber is only partially evacuated so that the target tissue is not dessicated during bombardment thereof. A vacuum of between about 400 to 800 millimeters of mercury is suitable.

Any target tissue capable of subsequent regeneration of shoot may be employed in practicing the present invention. The particular tissue chosen will vary depending on the clonal propagation systems available for, and best suited to, the particular species being transformed. Exemplary tissue targets include embryos, callus tissue, stems, existing meristematic tissue (e.g., apical meristems and root meristems), and induced meristem tissue (e.g., protocorm-like bodies). Preferred are tissues selected from the class consisting of meristematic tissue (both existing and induced) and the tissues capable of induction into meristematic tissue. More preferred are protocorm-like bodies. Target tissue is oriented for bombardment so that the microprojectile(s) enter one or more of the cells to be transformed. A preferred clonal propagation method for practicing the present invention is the method described below. This method comprises several steps: 1) treating excised apical meristems on a solid PLB induction medium for a time sufficient to induce formation of protocorm-like bodies on the tissue. 2) transferring the treated tissue to a liquid PLB proliferation medium to stimulate continued development of the meristematic tissues. 3) treating the protocorm-like bodies (PLBs) on a shoot regeneration medium for a time sufficient to induce formation of shoots. 4) transferring the treated shoots to a nutrient medium free of exogenous growth factors until the roots are developed. This method results in the production of propagules that may be transferred to and raised in soil to form adult plants.

The tissue culture system described immediately above provides developmental windows during which greater numbers of cells in the tissue being bombarded are in a specific phase of their cell cycle when they are more amenable to integration or expression of foreign DNA. Thus, the greater the proportion of cells in this phase in the tissue being bombarded, the higher the probability of obtaining stable expression in the bombarded tissue. The tissue is preferably bombarded with the DNA construct after the tissue has been treated on a liquid PLB proliferation medium for a time at least sufficient to induce the formation of superficial meristematic tissue from periclinal divisions of the first and second sub-epidermal cell layers on the target tissue. Also, the tissue is preferably bombarded with the DNA construct before it is transferred to a shoot regeneration medium for the production of shoots.

DNA coated onto the small carrier particles delivered into the cells is integrated into the genome DNA of some portion of the cells that are treated. Thereafter using appropriate selection or screening, whole tissues or organisms are generally regenerated from the transformed cells. In applying the general process of particle-mediated transformation of plant tissues to obtain transgenic plants, it is important to avoid regeneration of transgenic plants from chimeric tissues that comprise of both transformed and non-transformed cells. It is generally possible to obtain non-chimeric transgenic plants by bombarding genes into differentiated tissues, such as meristems, which subsequently can be regenerated directly into plantlets, as described in U.S. Pat. No. 5,015, 580. The present invention intends to stimulate continued development of meristematic tissues by culturing protocorm-like bodies in a liquid medium before particle bombardment, and to subject the proliferating meristematic tissues to particle bombardment. It is also found in the present invention that stably transformed orchid plants can be obtained by culturing the bombarded meristematic tissues in a combination of liquid and solid medium.

Use of dominant selectable markers is an integral part of transformation strategies. Important factors for efficient selection of transgenic cells are type of selectable markers, their expression level, and timing and intensity of selection after transformation (for review see Angenon et al., Angenon, et al., in Plant Molecular Biology Manual C1: 1–13, Kluwer Academic Publishers, Boston, Gelvin and Schilperoort, Eds, 1994). Markers available include genes encoding antibiotic-, antimetabolite-, and herbicide-resistance, and those conferring resistance to toxic levels of amino acids or analogs. Neomycin phosphotransferase II (NPTII) is the most widely used selectable marker for plant transformation. Through phosphorylation it inactivates aminoglycoside antibiotics such as kanamycin, neomycin, geneticin (G418), and paromocin. The sensitivity of plant cells to the selectable marker depends on the genotype; the physiological condition, size and type of explant; and tissue culture conditions. Therefore, the minimum level of a selection agent that can fully inhibit the growth of untransformed cells should be determined for each transformation and regeneration system. Kanamycin is generally used in concentrations from 50 to 200 mg/l. The selection can be skipped for a period sufficient to ensure prolific growth of the bombarded cells as the selection agent should effectively suppress the growth of untransformed cells while minimizing the toxicity of dying cells on neighboring transformed cells.

Screenable marker genes, by contrast, are genes coding for a product which is easy to detect, to thus screen for transgenic tissue. One useful screenable marker is the GUS, or beta-glucuronidase gene, for which a convenient colorometric assay system exists is used. Use of an intron containing GUS gene is generally preferred as the gene with intron is expressed only in eukaryotic (i.e., plant) cell, not in any contaminating microorganisms. GUS expression can be observed for both transient gene expression following particle-mediated transformation and stable gene expression from virtually all plant tissues after selective regeneration. The level of transient gene expression using the GUS assay system bears a general correlation with the efficacy of obtaining stable transformations, but the correlation is not a strong one. Once a plant or plantlet has been shown to have been transformed, the cells of the plant may then be used repeatedly for tissue culture, followed by the growth of plantlets. Thus the modified plant can be repeatedly regenerated by use of cell and tissue culture. In some instances, propagation may be maintained from seed, although monitoring for loss of the introduced gene would be advisable.

The following examples are offered by way of illustration and not of limitation. The description of key terminology used in the specific examples are as follow: Meristem—the undifferentiated plant tissue from which new cells arise; protocorm—a small storage organ derived from embryo possessing an apical meristem and a leaf primordium; protocorm like body (PLB)—tissue structure, derived from vegetative tissue, resembling seedling protocorm; primary PLBs—PLBs induced by culturing apical meristem-tip aseptically; secondary PLBs—PLBs formed on the surface of primary PLB in culture; proliferative PLBs—PLBs proliferating on the surface of the PLB explant including both primary and secondary PLBs.

EXAMPLE 1

Preparation of Cymbidium PLBs for Bombardment

Meristem-tips of the Cymbidium orchid were isolated in sterile condition and induced to form primary PLBs as described by Paek et al. Proc. NIOC, Nagoya, Japan (1997). The primary PLBs younger than twelve-month old were then maintained on Knudson Orchid medium (Duchefa Biochmie BV, Izaak Enchedeweg 40, 2031 CS Haarlem, The Netherlands) supplemented with 5% sucrose, 2 mg/l alpha-naphthalene acetic acid, 0.1% charcoal, and 0.7% Bacto-agar (pH 5.4). Before bombardment, the PLBs were cultured in a liquid medium with slow gyratory shaking (50 to 100 rpm) for the period of 7 to 10 days, and then placed in a circular area 1–2 cm in diameter on Knudson Orchid medium supplemented with 5% sucrose and 0.7% agar in a 60 mm Petri dish which served as the target surface. Controls (unbombarded tissue) were plated similarly. Incubation of all plant materials was at 25±2 degree(s) C. with 16 hr photoperiod under 25–45 uE/m sup 2 sec, using cool white fluorescent light.

EXAMPLE 2

Determining the Effect of Liquid Culture on PLB Proliferation Before Bombardment Three different culture techniques using Murashige and Skoog (MS), 15 Physiologia Plantarum 31 (1962), medium with 3% sucrose and without phytohormones; liquid culture with shaking, stationary liquid culture and solid culture; were used to induce the primary PLBs to form secondary PLBs before bombardment. For solid culture, forty PLBs were plated in a 125-mm Petri dish containing 25 ml MS medium supplemented with 0.7% agar. For liquid culture, forty PLBs were cultured in a 250-ml Earlymeyer-flask containing 50 ml MS liquid medium with or without shaking (50–100 rpm). Controls (unbombarded tissue) were plated similarly. The cultured PLBs were evaluated for production of secondary PLBs.

Figure 1:
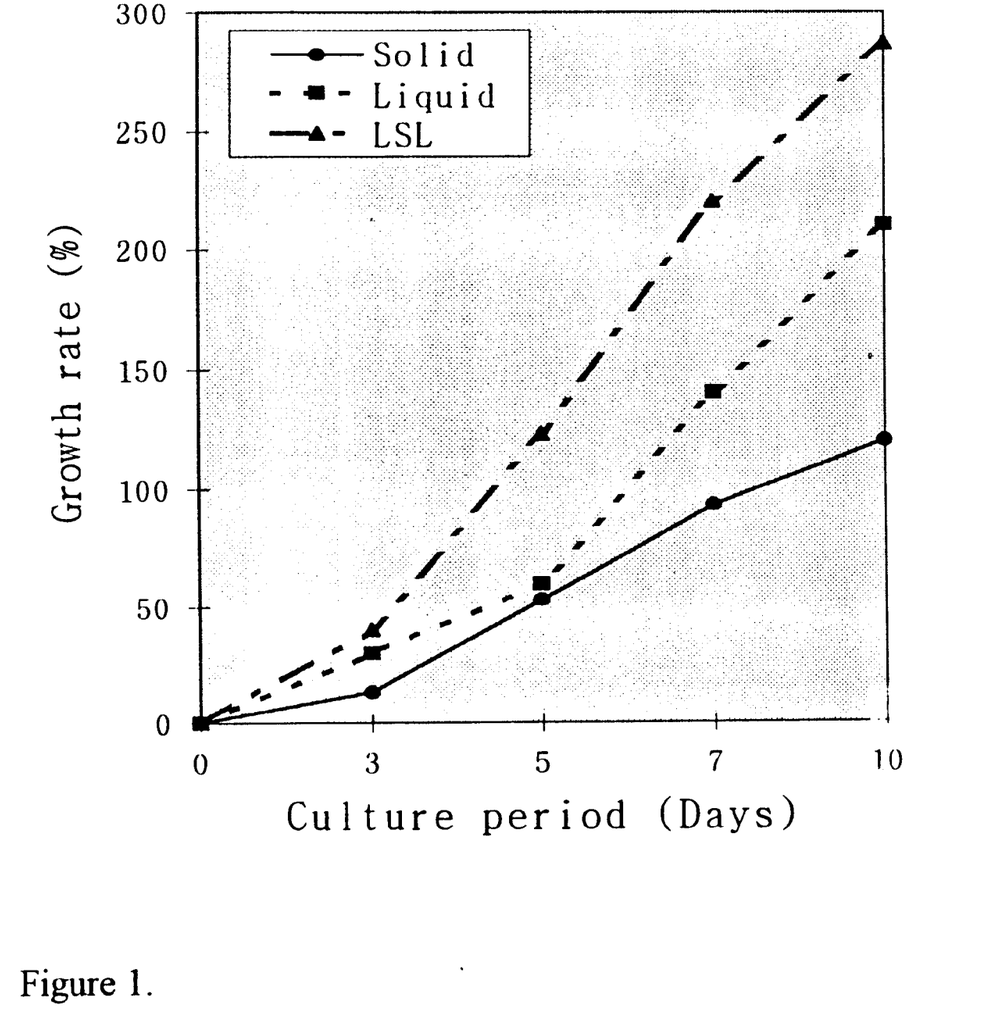
FIG. 1 illustrates the effects of three different culture techniques on PLB proliferation before particle bombardment.

FIG. 1 shows the data obtained from this procedure. The y-axis shows the rate of proliferation (mean number of PLBs multiplied per PLB), and the x-axis shows the days in culture before bombardment (or 'shooting'). Liquid culture with slow shaking yielded the highest proliferation of PLB.

EXAMPLE 3

Gene Construction

Figure 2:
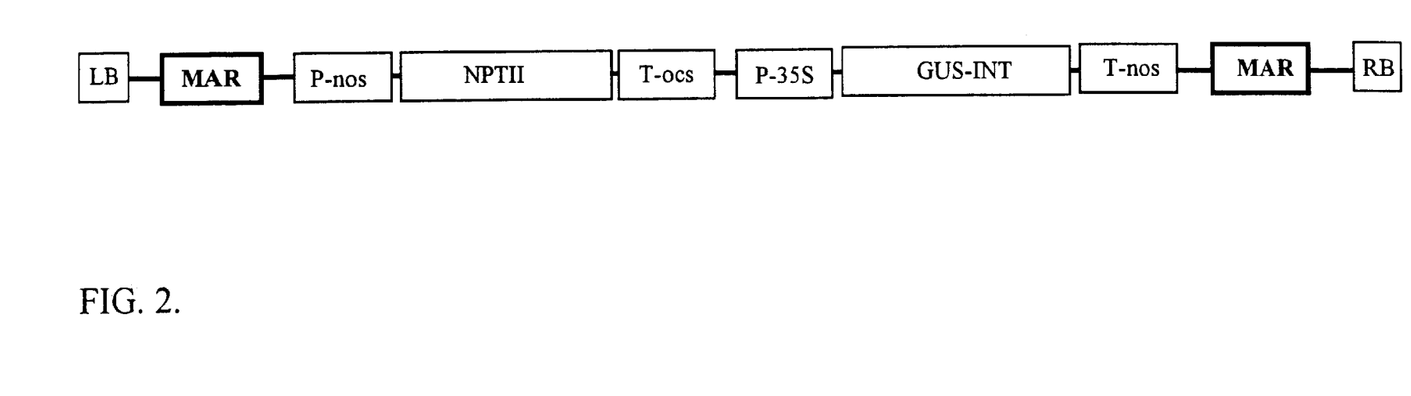
FIG. 2 is a schematic map of the T-DNA region of the plasmid pKH200. The relative position of the GUS-INT gene and the NPTII gene are flanked by the tobacco matrix regions (MARs).

The plant gene expression vector used in this example was pKH200, illustrated in FIG. 2 and by Han et al., Transgenic Research, 1997. This vector includes two separate plant expression cassettes for two different genes expressible in plant cells, in addition to one antibiotic resistance markers (kanamycin resistance), useful in bacterial hosts. One of the plant gene expression cassettes contains the gene NPT-II which confers resistance to the antibiotic kanamycin. Kanamycin has proven useful as a selectable marker in some plant species. The NPTII expression cassette includes a nopaline synthase promoter and octopine synthase polyadenylation sequence flanking the coding sequence. The second expression cassette codes for the beta-glucuronidase enzyme, or GUS, which serves as a screenable marker since its expression can be detected by convenient histochemical assay. The GUS gene is 3' to a cauliflower mosaic virus 35s promoter (CaMV35s) and 5' to a nopaline synthase polyadeylation region. The two expression cassettes are flanked by matrix attachment region (MAR) fragments derived from a tobacco genomic clone (Hall et al., Proc. Natl. Acad. Sci. USA, 1991).

EXAMPLE 4

Microprojectile Bombardment Parameters

Parameters used for the actual particle acceleration process were based on the use of a Model Biolistic PDS-1000/He (Bio-Rad Laboratories, 2000 Alfred Nobel Drive, Hercules, Calif. 94547) configured as described in the manual provided by the manufacturer. Stopping plates, rupture disks, and macroprojectiles were also supplied by Bio-Rad Laboratories. Plasmid DNA was precipitated in the presence of microprojectiles essentially as described by Klein et al., 327 Nature 70 (1987). Microprojectiles were prepared from gold particles with a diameter of approximately 0.6 mm. Each bombardment delivered approximately 500 ug of particles associated with 0.42 mg of plasmid DNA in a total slurry volume of 6 ml. DNA preparations used for microprojectile bombardments contained a mixture of supercoiled, open circle and linear molecules. The bombardment chamber was evacuated at a pressure of 28 inch of mercury. All bombardments were carried out with pressurized helium in the range of 1,100 to 1,550 psi, at a range of approximately 60 mm from the stopping plate to the surface of the treated tissue.

EXAMPLE 5

Tissue Culture After Bombardment

Tissue culture after bombardment is divided into two phases, proliferative PLB induction and selective culture: 1) the proliferative PLB induction—two (liquid vs solid) culture techniques were employed for the period of 10 to 45 days after bombardment using one-half strength of Murashige and Skoog, Physiologia Plantarum, 1962, medium with 3% sucrose and without phytohormones to promote proliferative PLB development. For solid culture, forty bombarded PLBs were plated in a 125-mm Petri-dish containing 25 ml MS medium supplemented with 0.7% agar. For liquid culture, forty bombarded PLBs were cultured in a 250-ml Earlymeyer-flask containing 50 ml MS liquid medium with or without shaking (50–100 rpm). The cultured PLBs were evaluated for production of ploriferative PLBs. Table 1 shows the results of this experiment. Liquid culture with slow shaking was better than solid culture in stimulating continued development of PLB. No kanamycin selection was used during the liquid culture. The culture techniques were evaluated for production of proliferative PLBs. 2) the selective culture—forty secondary PLBs having numerous proliferative PLBs on surface were transferred to a 125-mm Petri-dish containing 25 ml MS medium supplemented with 0.7% agar and 100–200 mg/l kanamycin. The cultures were maintained by weekly subculture to fresh medium. Growth room environmental conditions were identical to those used in EXAMPLE 1.

EXAMPLE 6

Assay of Bombarded Tissue for GUS Activity

Subsets of PLBs were sampled at various times to determine the frequency of beta-glucuronidase (GUS) activity. PLBs were incubated in substrate solution, containing 2.0 mM 5-bromo4-chloro-3-indoyl-beta-D-glucuronic acid (X-gluc), 0.1M NaPO sub 4 buffer, pH 7.0, 0.01M Na sub 2 EDTA, pH 7.0, 0.5 mM K sub 4 Fe(CN) sub 6 3H sub 2 O, pH 7.0, and 0.5 mM K sub 3 Fe(CN) sub 6 and 0.1% Triton X-100, for 18 hours at 37 degree(s) C. GUS foci on the PLBs were scored under a dissecting stereo-microscope.

Figure 3:
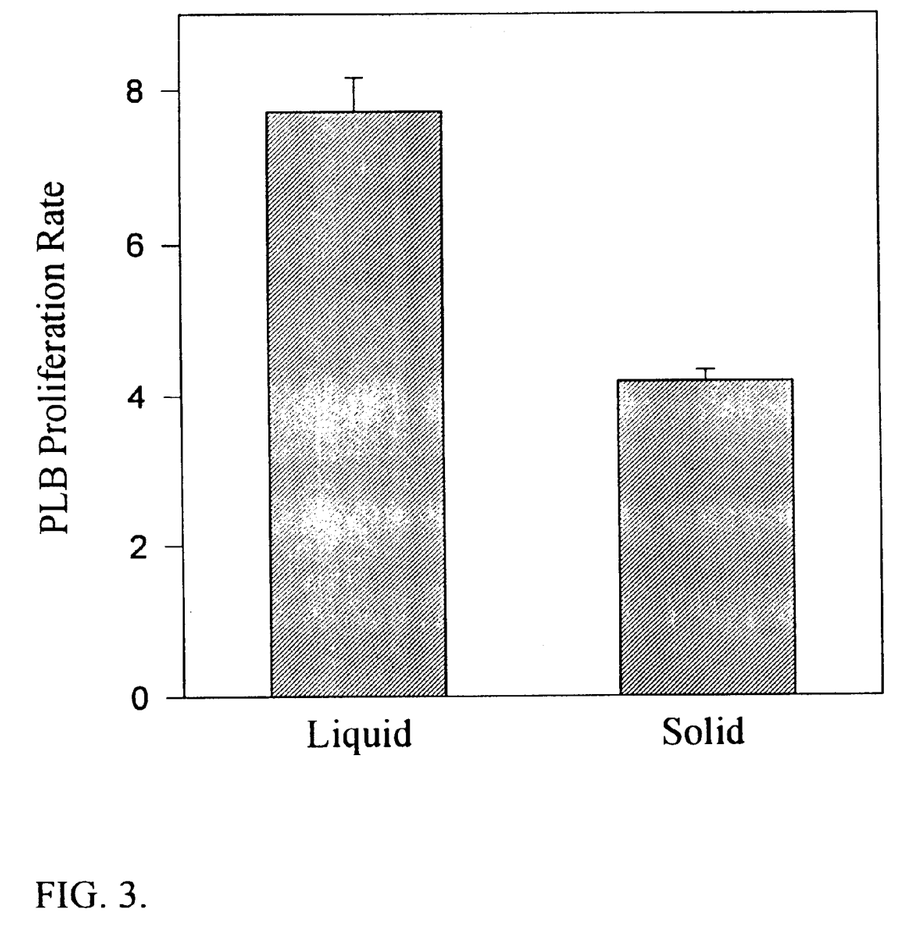
FIG. 3 is a chart illustrating the effect of two culture methods on PLB proliferation after bombardment.
Figure 4:
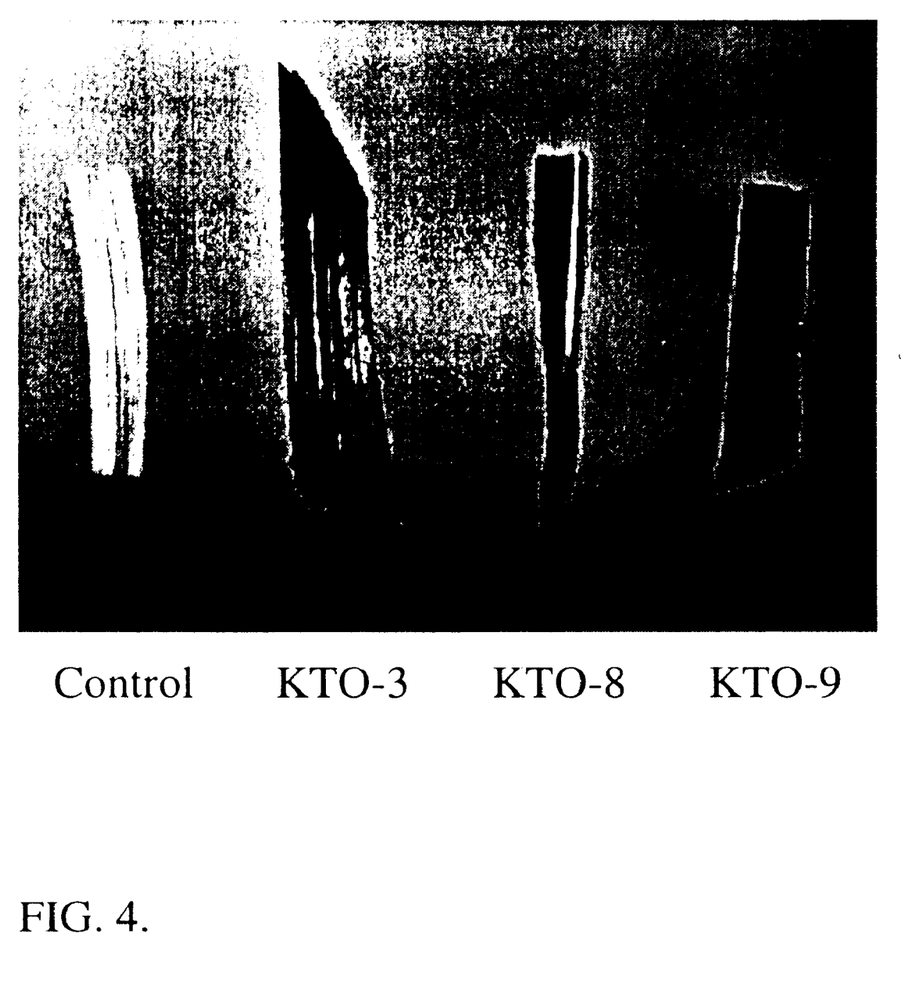
FIG. 4 is a chart illustrating the long-term and stable expression of the marker (GUS) gene in three transgenic orchid lines.
Figure 5:
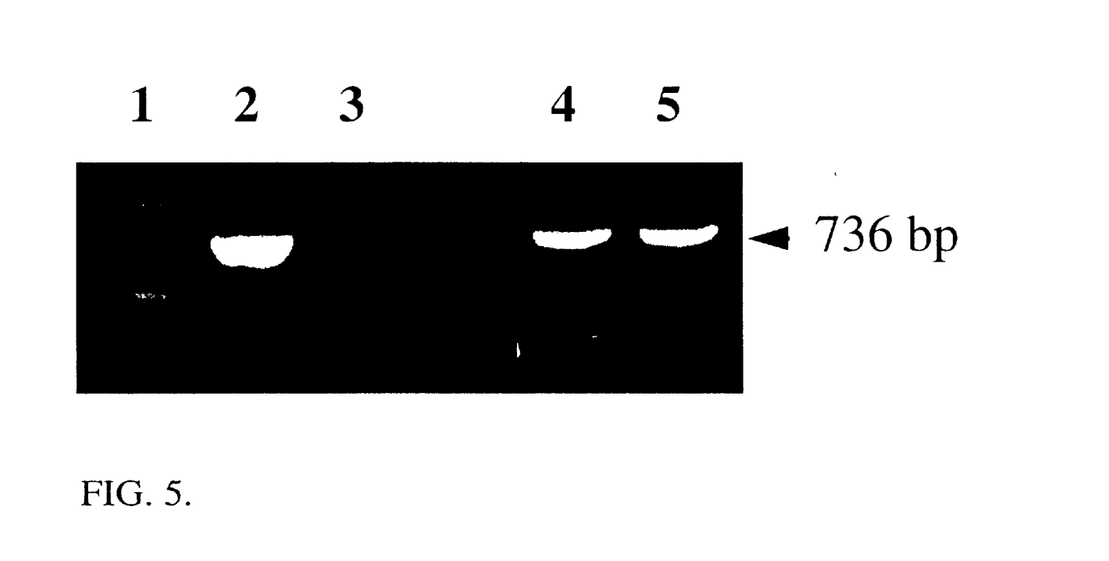
FIG. 5 illustrates the PCR amplified fragments of the introduced seletable marker (NPTII) gene from two transgenic orchid lines.

FIG. 3 illustrates in a graphical fashion the results achieved in repeated assays of the bombarded PLBs in an assay for transient GUS expression. The assay, which is destructive to the tissue, was conducted after 24, 48, 72 hours transformation.

EXAMPLE 7

Selection and Analysis of Transformed PLBs

To screen the relatively rare stable integration events from the transient activity, kanamycin selection was used. The PLBs cultured in liquid medium for the period of 10 to 45 days as described in EXAMPLE 5 were transferred to the same medium but supplemented 0.7% Bacto agar and 100 to 200 mg/l kanamycin for selection of transformed PLBs. The cultures on kanamycin were subcultured weekly to fresh medium to minimize the number of escapes due to the alleviated kanamycin toxicity. The transformed PLBs were identified initially by their ability to grow on kanamycin medium. Subsequently, stable integration and expression were confirmed by PCR analysis and GUS expression assay respectively. Literally hundreds of PLBs have been produced from successive PLB propagation. In excess of 100 of such PLBs survived the kanamycin selection. Over 20 plantlets were obtained from the kanamycin-resistant PLBs. Three randomly selected seedlings were sacrificed for GUS assay, and all three were all blue, indicating clonal expression. FIG. 3 shows GUS expression from bombarded PLBs. In essence, long-term and stable expression of the introduced foreign gene was achieved. It is expected that these plantlets will readily be cultivated into rooted orchids. Based on past experience with other plants, the inserted genes should generally segregate normally in the next generation and be inheritable through the normal rules of Mendelian inheritance. In general, the process is capable of reproducibly producing transformed PLB capable of giving rise to whole orchid plants.

TABLE 1

Effects of two different (liquid vs solid) culture methods on PLB proliferation after particle bombardment

| Culture Method[1] | PLB Proliferation Rate[2] |
|---|---|
| Liquid | 7.72 ± 0.44 |
| Solid | 4.20 ± 0.14 |

What is claimed is:

1. A method of genetically engineering an orchid with a DNA construct comprising an expression cassette, which construct comprises, in the 5' to 3' direction, a transcription initiation region and a peptide coding region positioned downstream from said transcription initiation region and under the transcriptional regulation thereof, said method comprising the steps of:
   (a) culturing primary protocorm-like bodies (PLBs) of the orchid in liquid medium to induce secondary PLBs;
   (b) placing the PLBs comprising both primary and secondary PLBs on a target surface;
   (c) physically accelerating at the PLBs microprojectiles which comprise copies of a foreign genetic construct comprising at least one foreign gene of interest and at least one selectable marker gene;
   (d) culturing the PLBs from (c) in liquid medium to form proliferative PLBs;
   (e) inducing the proliferative PLBs to form shoots in liquid medium containing at least one selection agent for which the at least one selectable marker gene confers resistance, imparts prototrophy or imparts a visible phenotype to the proliferative PLB in the presence of the selection agent to form selectable PLBs having shoots, said selectable PLBs being transformed plant tissue;
   (f) culturing selectable PLBs which have shoots; and
   (g) regenerating the shoots of the selectable PLBs into clonal transgenic orchid plants wherein, said orchid is a member of genus Cymbidium.

2. A method as claimed in claim 1, wherein said primary PLB comprises meristematic tissue and tissue that is inducible to develop into meristematic tissue and regenerate into a plant or plantlet.

3. A method as claimed in claim 1, wherein said primary PLB comprises meristematic tissue derived from apical meristems of the orchid, and tissue that is inducible to develop into secondary PLB and regenerate into a plant or plantlet.

4. A method as claimed in claim 1, wherein said secondary PLB comprises meristematic tissue derived from the primary PLB of the orchid, and tissue that is inducible to develop into proliferative PLB and regenerate into a plant or plantlet.

5. A method as claimed in claim 1, wherein said proliferative PLB comprises meristematic tissue derived from the PLB explant comprising both primary and secondary PLBs of the orchid, and tissue that is inducible to regenerate into a plant or plantlet.

6. A method as claimed in claim 1, wherein said selectable marker gene codes for the expression of an antibiotic resistance trait.

7. A method as claimed in claim 1, wherein said microprojectile comprises a metallic particle having a diameter of from about one-half micrometer to about three micrometers.

8. A method according to claim 1, wherein a plurality of said microprojectiles is provided, each of said microprojectiles having said foreign genetic construct immobilized thereon, and each of said microprojectiles being propelled at said plant tissue target.

9. A method according to claim 1, further comprising the step of generating roots from said transformed plant tissue.

10. A method as claimed in claim 1, wherein the selection agent is kanamycin.

* * * * *